United States Patent

Chai et al.

(10) Patent No.: US 6,444,694 B1
(45) Date of Patent: Sep. 3, 2002

(54) STYRYL BENZIMIDAZOLE DERIVATIVES

(75) Inventors: Sie-Yearl Chai, Lawrenceville, NJ (US); Hassan M. Elokdah, Fairless Hills; Theodore S. Sulkowski, Wayne, both of PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 08/468,271

(22) Filed: Jun. 6, 1995

(51) Int. Cl.$^7$ .................... A61K 31/415; C07D 235/26; C07D 235/22; C07D 235/12
(52) U.S. Cl. ................ 514/394; 548/309.7; 548/310.1; 548/310.4
(58) Field of Search ........................... 548/309.7, 310.1, 548/310.4; 514/394

(56) References Cited

U.S. PATENT DOCUMENTS

| 5,026,705 A | 6/1991 | Prucher et al. |
| 5,196,446 A | 3/1993 | Levitzki et al. |
| 5,387,600 A | 2/1995 | Aikawa et al. |

FOREIGN PATENT DOCUMENTS

| DE | 4212748 | 10/1993 |
| FR | 1576989 | * 4/1969 |
| WO | 9116305 | 10/1991 |

OTHER PUBLICATIONS

Sullivan, "New Benzimidazoles" CA 73:45408n (1970).*
Tkachev et al., "Luminescence and Scintillation, etc" CA 63:7788e (1965).*
Pushkina et al., "Syntheses of Benzimidazoles, etc" CA 58:9050d (1963).*
Farbwerke Hoechst A–G, "Benzimidazole Fluorescent, etc" CA 74:4702f (1971).*
Bailstein Ref: 5–23 –12–00473 (1970).*
Muir et al., "Synthesis and Characterization, etc" Inorganica Chimica Acta, 191 (1992) 131–139.*
Inoue et al., "1–Benzyl–Substituted, etc" CA 82:57696d (1975).*
Ricoh Co., Ltd., "Photosensitive Drum for, etc" CA 102:140734s (1985).*
Sullivan, "New Benzimidazoles", *J. Med. Chem.*, 1970, 13 (4), 784–6.*
Tkachev et al., "Luminescence and Scintillation, etc", Zh. Prikl. Spektroskopii, *Akad Nauk Belorussk.* SSR, 2(1), 63–65 (1965).*
Efros et al., Chem. Het. Comp (Engl. Transl) 6, 1970, 937.*
Pol. J. Pharmacol. Pharm., 33, 217–221, 1981.

* cited by examiner

*Primary Examiner*—Patricia L. Morris
(74) *Attorney, Agent, or Firm*—Rebecca R. Barrett

(57) ABSTRACT

Disclosed herein are compounds of the formula:

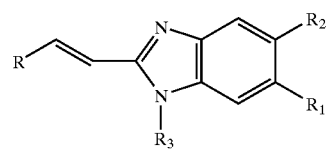

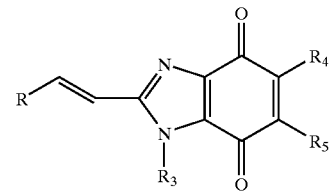

wherein
R is phenyl or substituted phenyl;
or R is furyl, pyridyl or quinolinyl;
$R_1$ and $R_2$ are hydrogen, halogen, alkyl, alkoxy, nitro, carboxyl, alkoxy-carbonyl or aryloxycarbonyl;
$R_3$ is hydrogen, alkyl, aryl or arylalkyl;
$R_4$ and $R_5$ are hydrogen or alkyl;
or a pharmaceutically acceptable salt thereof, which are useful as inhibitors of smooth muscle cell proliferation.

11 Claims, No Drawings

STYRYL BENZIMIDAZOLE DERIVATIVES

BACKGROUND OF THE INVENTION

Proliferation and directed migration of vascular smooth muscle cells are important vascular occlusive components in such processes as hypertension-induced vascular remodeling, vascular restenosis, and atherosclerosis (Gibbons, G. H.; Dzau, V. J.; NEJM, 1994; 330: 1431). The overall disease process is referred to as hyperproliferative vascular disease based on the etiology of the disease process. Vascular occlusion is preceded by stenosis resulting from intimal smooth muscle cell hyperplasia (Clowes, A. W.; Reidy, M. A.; J. Vasc. Surg., 1991, 13: 885). The underlying cause of intimal smooth muscle cell hyperplasia is vascular smooth muscle cell injury leading to disruption of the endothelium and extracellular matrix (Schwartz, S. M., Human Pathology, 1987; 18: 240; Fingerle, J., Arteriosclerosis, 1990; 10: 1082). Normally, the cells of the arterial wall are under close negative control and in a low basal proliferating state or in a quiescent non-proliferating state. Following vascular injury, the release of growth factors and cytokines result in smooth muscle cell proliferation and migration (Fagin, J. A.; Forrester, J. S., Trends in Cardiovascular Med., 1992; 2; 90.; Shiratani, M.; Yui, Y.; Kawai, C., Endothelium, 1993; 1: 5).

Vascular injury leading to intimal hyperplasia can be induced immunologically or by invasive cardiovascular procedures. Atherosclerosis is a common form of biologically mediated vascular injury progressing to stenosis. Abnormal proliferation of vascular smooth muscle cells is a feature of atherosclerotic plaques responsible for obstructive neo-intimal lesions at the site of intimal damage (Ross, R., Nature, 1993: 362; 801; Cascells, W., Circulation, 1992; 86: 723). Mechanical injury leading to intimal hyperplasia can occur following angioplasty procedures, organ transplant surgery and other vascular invasive procedures that disrupt vascular integrity (Clowes, A. W.; Reidy, M. A., J. Vasc. Surg., 1991; 13: 885; Isik, F. F.; McDonald, T. O.; Ferguson, M.; Yanaka, E., Am. J. Pathol., 1992; 141: 1139).

Percutaneous transluminal coronary angioplasty has achieved wide acceptance for the treatment of coronary artery stenosis. In this procedure the endothelium is damaged and exposed to a variety of chemoattractants and mitogens which are either blood-borne or are released at the site of injury. Among these agents, platelet-derived growth factor (PDGF) is thought to play a significant role in the process of smooth muscle cell proliferation and chemotaxis (Reidy, M. A.; Fingerle, J.; Lindner, V.; Circulation, 1993: 86 (suppl III): III-43.; Ferns, G. A. A.; Raines, E. W.; Sprugel, K. H.; Montani, A. S.; Reidy, M. A.; Ross, R.; Science, 1991; 253: 1129.; Jawien, A., et al., J. Clin. Invest., 1992; 89: 507; Nabel, E. G., et al., J. Clin. Invest., 1993; 91: 1822). Within 3 to 6 months after angioplasty, a significant reduction in blood flow occurs in approximately 30–40% of patients as a result of restenosis caused by response to vascular injury during this procedure. These patients then require a second interventional procedure (Pepine, C., Circulation, 1990; 81: 1753.; Hardoff, R. J., J. Am. Coll. Cardiol., 1990; 15: 1486). Accordingly, agents that limit the restenosis process would be of significant benefit. Agents that inhibit vascular smooth muscle cell proliferation, particularly PDGF-stimulated proliferation, would be useful in the treatment of vascular hyperproliferative disorders (Molloy, C. J., Drug Dev. Res., 1993; 29: 148.; Newby, A. C.; George, S. J., Cardiovasc. Res., 1993; 27: 1173).

DE 4, 129, 603 discloses fused heterocyclic compounds (benzimidazoles) as inhibitors of collagen-induced platelet aggregation and fibrinogen, that may also be useful in the "treatment of transluminal angioplasty". U.S. Pat. No. 5,387,600 discloses 2-thio substituted benzimidazoles for the treatment of atherosclerosis. U.S. Pat. No. 5,026,705 discloses 2-styryl benzimidazolyl pyridazinones as positive inotropic agents useful in the treatment of congestive heart failure.

The tuberculostatic activity of 2-[α-cyano-β-aryl vinyl] benzimidazole derivatives has been disclosed in Pol. J. Pharmacol. Pharm., 1981, 33, 217 (CA 96: 293). WO 9116305 discloses diheterocyclic propene nitrile derivatives as cellular antiproliferative agents. U.S. Pat. No. 5,196,446 discloses indolyl propenenitriles as cellular antiproliferative agents.

DESCRIPTION OF THE INVENTION

In accordance with this invention, there is provided a group of styryl benzimidazoles of formula I and styryl benzimidazoldiones of formula II

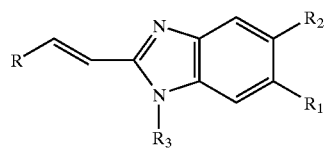

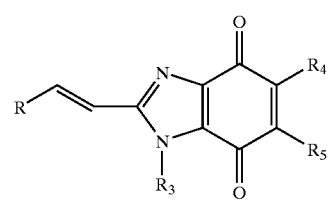

wherein R is phenyl or phenyl substituted with halogen, hydroxyl, alkoxy of 1 to 6 carbon atoms, alkyl of 1 to 6 carbon atoms, trifluoromethyl, or R is furyl, pyridyl or quinolinyl; $R_1$ and $R_2$ are hydrogen, halogen, alkyl of 1 to 6 carbon atoms, alkoxy of 1 to 6 carbon atoms, nitro, carboxyl, alkoxycarbonyl of 2 to 7 carbon atoms or aryloxycarbonyl of 7 to 12 carbon atoms; $R_3$ is hydrogen, alkyl of 1 to 6 carbon atoms, aryl of 6 to 12 carbon atoms or arylalkyl of 7 to 12 carbon atoms; $R_4$ and $R_5$ are hydrogen or alkyl of 1 to 6 carbon atoms; or a pharmaceutically acceptable salt thereof.

The compounds of the present invention are prepared according to the general sequence of reactions outlined in the scheme below.

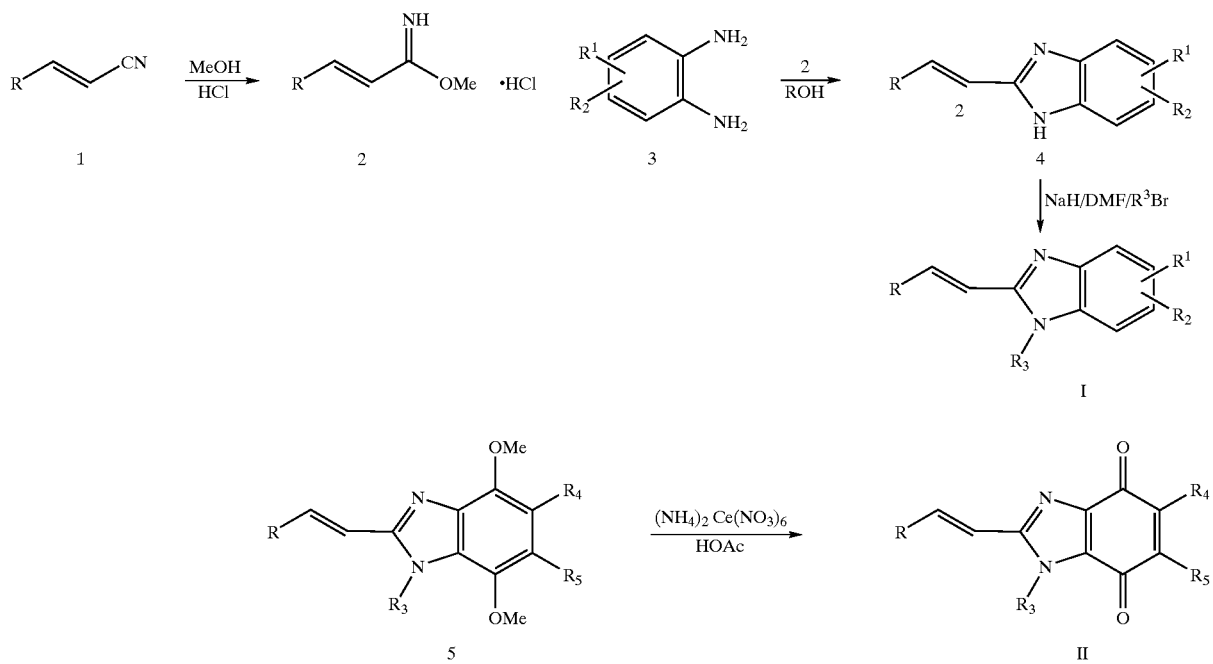

The iminoether hydrochloride (2) is prepared by reacting an appropriate nitrile with an alcohol and excess hydrogen chloride at 0° C. Reaction of (2) and an appropriate 1,2-diaminobenzene in refluxing ethanol affords the corresponding 2-styryl benzimidazole (4). Alkylation of (4) with an alkyl, aryl or arylalkyl halide in dimethyl formamide using sodium hydride as base affords compounds of formula I. Compounds of formula II are obtained by oxidation of 1,4-dimethoxy derivatives of formula I with ammonium cesium nitrate. Two equivalents of ammonium cesium nitrate are dissolved in 1:4 water/acetonitrile and added dropwise to a solution of an appropriate 1,4-dimethoxy styrylbenzimidazole and acetic acid. The mixture is heated at 40° C. for 1 hour to obtain compounds of formula II.

The pharmaceutically acceptable acid addition salts are those derived from such organic and inorganic acids as: acetic, lactic, citric, fumaric, tartaric, succinic, maleic, malonic, hydrochloric, hydrobromic, phosphoric, nitric, sulfuric, methanesulfonic, methylbenzene sulfonic, and similarly known acceptable acids. With those compounds possessing an acidic substituent such as the carboxylic acids, the pharmaceutically acceptable salts include the alkali metal salts (sodium or potassium), the alkaline earth metal salts (calcium or magnesium) and ammonium salts.

This invention includes pharmaceutical compositions comprised of styryl benzimidazoles either alone or in combination with excipients (i.e. pharmaceutically acceptable materials with no pharmacological effect). Such compositions are useful for diseases which are characterized by excessive smooth muscle cell proliferation most frequently arising from vascular reconstructive surgery and transplantation, for example, balloon angioplasty, vascular graft surgery, coronary artery bypass surgery, and heart transplantation. Other disease states in which there is unwanted vascular proliferation include hypertension, asthma, and congestive heart failure. The compounds of this invention are thus useful for treating these diseases and states.

The compounds of this invention may be administered systemically, for example by intravenous injection, typically ranging from 0.1 to 10 mg/kg/h over 5–30 days, or by subcutaneous injection at lower dose, by oral administration at higher dose than intravenous injection. Localized delivery of the compounds of this invention may also be achieved by transmembrane, transdermal, or other topical administrative routes using appropriate continuous release devices such as supporting matrix, where applicable. The compositions of the invention may be formulated with conventional excipients, such as a filler, a disintegrating agent, a binder, a lubricant, a flavoring agent and the like. These are formulated in a conventional manner.

The compounds may be administered neat or with a solid or liquid pharmaceutical carrier to a patient in need of such treatment. Applicable solid carriers can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form. Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific patient suffering from a disease involving smooth muscle cell proliferation must be subjectively determined by the attending physician. The variables involved include the specific disease state and the size, age and response pattern of the patient.

The ability of the compounds of the present invention to inhibit smooth muscle cell proliferation was established using isolated porcine aortic smooth muscle cells in a modification of the procedure of Castellot et al. J. Biol. Chem 257(19) 11256 (1982), as follows:

Fresh porcine aortas, scrupulously cleansed of fatty tissue, are rinsed in sterile phosphate-buffered saline with 2% antibiotic-antimycotic (100×) liquid (10,000 units of penicillin (base), 10,000 $\mu$g of streptomycin (base), and 25 $\mu$g of amphotericin B/mL utilizing penicillin G (sodium salt), streptomycin sulfate, and amphotericin B as Fungizone® in 0.85% saline, available from Gibco Laboratories, Grand Island Biological Co., Grand Island, N.Y.). The tissue is then digested in 10–15 mL of an enzyme solution containing collagenase type I, 165 U/mL; elastase type III, 15 U/mL; BSA, 2 mg/mL; and soybean trypsin inhibitor, 0.375 mg/mL, followed by incubation at 37° C. under 5% $CO_2$ atmosphere for 10 to 15 minutes. After this treatment, the outer surface adventitia is removed by peeling with a forceps. The aorta is then longitudinally cut and laid open and the endothelial layer is removed by scraping.

The medial layer of cells is rinsed in the enzyme solution, and placed in a new 100 mm dish with 10 mL of enzyme solution. The medial layer of cells is minced using a fine pair of scissors and digested for 2–3 hours at 37° C. in 30 mL of fresh enzyme solution. After digestion, the medial tissue is homogenized using a sterile Pasteur pipette with a fire polished tip or an Eppendorf pipetter with a 200–1000 $\mu$L sterile pipette tip. The suspension is then centrifuged for 10 minutes at 8000 rpm and the pellet is suspended in 4–6 mL of fresh enzyme solution and plated onto 4–6 100 mm flasks with vented caps. The cells are then allowed to grow to confluence and split using 0.25% trypsin. The cells are evaluated for purity and overall quality using antibody to SMC actin.

The cells are assayed in early passage (generally passage 3–7) at sub-confluent conditions. Cultures are grown in 16 mm (24 well) multi-well culture dishes in media 199 supplemented with 10% fetal bovine serum and 2% antibiotic/antimycotic. At subconfluence, the cells are placed in a defined serum free, lymphocyte medium (AIM-V; Gibco) for 24–48 hours prior to initiating the experimental protocol.

The standard test procedure is initiated by addition of the test compound, $^3$H thymidine and serum or a specific growth factor to the serum deprived synchronized cells. Growth factor and serum stimulations are optimized for each cell type. The test compounds are added to each well at 50 fold dilution (20 $\mu$L/well) and the plates are incubated for 24–36 hours at 37° C. in 5% $CO_2$ atmosphere. Test compounds are dissolved in 50% ethanol and assayed at 1, 10, and 100 $\mu$M. As a control, RG 50872 (Bilder, G. A.; et al., Am. J. Cell Physiol., 1991; 260: C721) is routinely assayed under the conditions of each cell preparation at a concentration of 5 $\mu$M.

At the completion of the experiment, the plates are placed on ice, washed three times with ice cold PBS and incubated in ice cold 10% trichloroacetic acid (TCA) for 30 minutes to remove acid soluble proteins. Each solution is transferred to a scintillation vial containing 0.4N HCl (500 $\mu$L/vial to neutralize NaOH) and each well is rinsed two times with water (500 mL) for a total volume of 2 $\mu$L/vial.

Data is quantitated by subjecting the vials to a scintillation counter, in triplicate, for both control and experimental samples. Control (100%) data is obtained from maximally stimulated cells, as the result of growth factor or serum stimulation. Experimental data is obtained from cells maximally stimulated with growth factor or serum and treated with a test compound. (The platelet-derived growth factor used in the assay was human recombinant PDGF-AB purchased from Upstate Biotechnology Inc., Lake Placid, N.Y.). Data is expressed as a percent of control from which $IC_{50}$s are determined.

To distinguish cytotoxicity from the ability of a compound to prevent proliferation, the test compounds were examined using a commercial modification of the MTT assay. Briefly, cells were grown in 24 well plates to 70–80% confluency. The cells were serum deprived for 24–48 hours prior to initiation of the experimental protocol. To insure that the MTT assay monitored toxicity rather than proliferation, the cells were incubated with 50 mM test compound in fresh medium without serum for 24 hours at 37° C. in a humidified $CO_2$ incubator. Upon completion of the compound treatment, MTT indicator dye was added for 4 hours a 37° C. Cells were then solubilized and aliquots from each will were transferred to a 96-well plate for analysis. Absorbance at 570 nm wavelength with a reference wavelength of 630 nm was recorded using an ELISA plate reader. Results are reported as percent viable using no drug (100% viable) and pre-solubilization (0% viable) standards.

The compounds of the present invention are effective inhibitors of smooth muscle cell proliferation as shown by the data presented in Table I.

TABLE I

| Compound of Example Number | Porcine Smooth Muscle Cell Antiproliferation $IC_{50}$ or % Inhibition at x Concentration | | Cytotoxicity |
|---|---|---|---|
| | Serum | PDGF | % Viable Cells |
| 1 | 5.91 $\mu$M | 4.1 $\mu$M | 100 |
| 2 | 11.4 $\mu$M | 3.48 $\mu$M | 100 |
| 3 | 7.6 $\mu$M | 0.324–0.801 $\mu$M | 100 |
| 4 | 1.28 $\mu$M | 1.5 $\mu$M | 100 |

TABLE I-continued

| Compound of Example Number | Porcine Smooth Muscle Cell Antiproliferation IC$_{50}$ or % Inhibition at x Concentration | | Cytotoxicity |
|---|---|---|---|
| | Serum | PDGF | % Viable Cells |
| 5 | 1.2 μM | 6.12 μM | 100 |
| 6 | 2.26 μM | 7.49 μM | 100 |
| 7 | 0.567–1.9 μM | 1.49 μM | 100 |
| 8 | 0.915–10.2 μM | 0.622 μM | 80 |
| 9 | 14.5 μM | 0.858 μM | 100 |
| 10 | 8.36 μM | 0.62 μM | 45 |
| 11 | 1.36 μM | 0.06 μM | 100 |

The following examples are provided by way of illustration rather than limitation, for representative compounds of the invention and methods for their production.

EXAMPLE 1

Step 1

Methyl-(3,4-dimethoxy)-cinnamoimidate hydrochloride

A suspension of 3,4-dimethoxycinnamonitrile (10 g; 52 mmol) in EtOH (150 mL) was cooled in an ice bath. The cold mixture was then saturated with hydrogen chloride. The reaction solution was refrigerated for 18 hours. The precipitate formed was collected by filtration. The colorless solid gave 8.0 g (60% yield) of methyl-(3,4-dimethoxy)-cinnamoimidate hydrochloride which was used in the next reaction, $^1$H-NMR (DMSO-d$_6$; 200 MHz) δ11.8 (broad s, 1H), 10.9 (broad s, 1H), 7.82–7.9 (d, 1H), 7.3 (d, 2H), 7.02–7.12 (d, 1H), 6.81–6.9 (d, 1H), 4.2 (s, 3H), and 3.76 (s, 3H), 3.82 ppm (s, 3H).

Step 2

(E)-2-[2-(3,4-Dimethoxyphenyl)-vinyl]-1H-benzoimidazole

A mixture of 1,2-phenylenediamine (0.63 g; 5.8 mmol) and methyl-(3,4-dimethoxy)-cinnamoimidate hydrochloride (1.5 g; 5.8 mmol) in methanol (35 mL) was stirred at ambient temperature for 18 hours. The methanol solution was concentrated to dryness. The residue was recrystallized from MeOH-Diethyl Ether to obtain 1.3 g (67% yield) of the title compound as a mono-hydrochloride, hydrate, yellow solid, m.p. 248° C. dec. Anal. Calcd. for C$_{17}$H$_{16}$N$_2$O$_2$ HCl H$_2$O: C, 60.98, H, 5.12; N, 8.37. Found: C, 60.78; H, 5.12; N, 8.45. Mass Spectrum: (EI; M$^+$) m/z 280..$^1$H-NMR (DMSO-d$_6$; 400 MHz) δ15.2 (broad s, 1H), 8.18–8.2 (d, 1H), 7.76–7.8 (m, 2H), 7.45–7.54 (m, 2H), 7.32 (d 1H), 7.2–7.3 (m, 3H), 7.08–7.12 (d, 1H), 3.83 (s, 3H), 3.86 ppm (s, 3H).

EXAMPLE 2

2-[2-(3,4-Dimethoxyphenyl)-vinyl]-5-methoxy-1H-benzoimidazole

A mixture of 4-methoxy-1,2-phenylenediamine dihydrochloride (1.55 g; 7.3 mmol) and methyl-(3,4-dimethoxy)-cinnamoimidate hydrochloride (1.9 g; 7.3 mmol) in methanol (50 mL) was stirred at ambient temperature for 72 hours. The methanol was concentrated to 25 mL. A yellow solid was separated by filtration. The solid was suspended in MeOH (10 mL), and treated with hydrogen chloride. The precipitate that formed was collected to obtain 515 mg (21% yield) of the title compound as a mono-hydrochloride, hydrate, yellow solid, m.p. 246–249° C. Anal. Calcd. for C$_{18}$H$_{18}$N$_2$O$_3$HCl. H$_2$O: C, 61.72, H, 5.20; N, 7.79. Found: C, 61.61; H, 5.37; N, 7.84 . Mass spectrum: (EI; M$^+$) m/z 310. $^1$H-NMR (DMSO-d$_6$; 400 MHz) δ14.8 (broad s,1H), 8.3–8.5(d,1H), 7.62–7.63 (d, 1H), 7.3 (d,1H), 7.21–7.23 (dd 1H), 7.2 (d, 2H), 7.07–7.16(m, 3H), 3.86–3.88 (d, 6H), 3.82–3.84 ppm (s, 3H).

EXAMPLE 3

{2-[2-(3,4-Dimethoxyphenyl)-vinyl]-1H-benzoinmidazol-5-yl}-phenyl-methanone

A mixture of 3,4-diaminobenzophenone (1.7 g; 8.0 mmol) and methyl-(3,4-dimethoxy)-cinnamoimidate hydrochloride (2.0 g; 8.0 mmol) in methanol (50 mL) was stirred at ambient temperature for 48 hours. The methanol was concentrated to 25 mL. A yellow precipitate that formed was separated by filtration. Recrystallized from MeOH afforded 1.14 g (37% yield) of the title compound as a yellow solid, m.p. 211–214° C. Anal. Calcd. for C$_{24}$H$_{20}$N$_2$O$_3$: C, 74.98, H, 5.24; N, 7.29. Found: C, 74.88; H, 5.12; N, 7.23. Mass spectrum: (FAB,M+H) m/z 385. $^1$H-NMR (DMSO-d$_6$; 400 MHz) δ12.9–13.0 (broad s,1H), 7.9 (s, 1H), 7.73–7.77 (d,2H), 7.64–7.69 (m, 4H), 7.55–7.6 (t, 2H), 7.3 (s, 1H), 7.16–7.22 (d, 2H), 7.0 (d, 1H), 3.83 (s, 3H), 3.8 ppm (s, 3H).

EXAMPLE 4

Step 1

2,3-Dimethyl-5,6-dinitro-1,4-dimethoxybenzene

A solution of 2,3-dimethyl-1,4-dimethoxybenzene (16.6 g; o.1 mol) in acetic acid (100 mL) was cooled in an ice bath, then conc. HNO$_3$ (40 mL) was added dropwise over 15 minutes. After the addition, the reaction mixture was stirred at ambient temperature for 3 hours, then heated at 50° C. for 20 minutes. Solution was concentrated to 75 mL under vacuum, then poured into ice-H$_2$O (350 mL). The yellow precipitate (8.1 g) was collected. Recrystallization from EtOH gave 5.4 g (18.5% yield) of 2,3-dimethyl-5,6-dinitro-1,4-dimethoxybenzene as a yellow solid, m.p. 147–150° C.

Step 2

2,3-Dimethyl-5,6-diamino-1,4-dimethoxybenzene 2,3-Dimethyl-5,6-dinitro-1,4-dimethoxybenzene (4.0 g; 15 mmol) in EtOH (120 mL) was heated to solution, and 10% palladium on charcoal (1.0 g) was added.. The reaction mixture was hydrogenated at 45 psig for 3 hours. After work-up, 2.41 g (83% yield) of 2,3-dimethyl-5,6-diamino-1,4-dimethoxybenzene was obtained as a yellow solid, m.p. 107–110° C.

Step 3

2-[2-(3,4-Dimethoxyphenyl)-vinyl]-4,7-dimethoxy-5,6-dimethyl-1H-benzoimidazole

A mixture of 2,3-dimethyl-5,6-diamino-1,4-dimethoxybenzene (2.57 g; 10 mmol) and methyl-(3,4-dimethoxy)-cinnamoimidate hydrochloride (1.96 g; 10 mmol) in methanol (35 mL) was stirred at ambient temperature for 18 hours. The methanol solution was concentrated to 15 mL. The yellow precipitate was separated by filtration. Recrystallization from MeOH afforded 2.1 g (58% yield) of the title compound as yellow solid, m.p. 116–119° C. Anal. Calcd. for $C_{21}H_{24}N_2O_4$: C, 66.46, H, 6.57; N, 7.60. Found: C, 66.83; H, 6.64; N, 7.41. Mass spectrum: (EI,M$^+$) m/z 368 $^1$H-NMR (DMSO-d$_6$; 400 MHz) δ12.4–12.5(broad s,1H), 7.6–7.4 (d, 1H), 7.2 (d, 1H), 7.07–7.16 (m, 2H), 7.0 (d, 1H), 3.84(s, 3H), 3.78 (s, 3H), 2.2 ppm (s, 3H).

EXAMPLE 5

(E)-2-[2-(3,4-Dimethoxyphenyl)-vinyl]-1H-benzoimidazole-5-carboxylic acid methyl ester A mixture of 1,2-diamino-4-methylcarboxybenzene (3.6 g; 20 mmol) and methyl-(3,4-dimethoxy)-cinnamoimidate hydrochloride (5.4 g; 20 mmol) in methanol (150 mL) was stirred at ambient temperature for 48 hours. Solution was concentrated to dryness. The residue was recrystallized from MeOH to obtain 3.8 g (56% yield) of the title compound as yellow solid, m.p. 185–188° C. Anal. Calcd. for $C_{19}H_{18}N_2O_4$: C, 67.45, H, 5.36; N, 8.28. Found: C, 67.25; H, 5.45; N, 8.28. Mass Spectrum: (EI; M$_+$) m/z 338. $^1$H-NMR (DMSO-d$_6$; 400 MHz) δ12.9 (broad s, 1H), 8.1 (s, 1H), 7.63–7.69 (d, 1H), 7.57–7.62 (d, 1H), 7.33 (d, 1H), 7.17–7.21 (dd 1H), 7.14–7.19 (d, 1H), 7.08–7.12 (d, 1H), 3.86 (s, 3H), 3.84 (s, 3H), 3.79 ppm (s, 3H)

EXAMPLE 6

(E)-2-[2-(3,4-Dimethoxyphenyl)-vinyl]-1H-benzoimidazole-5-carboxylic acid

A mixture of 2-[2-(3,4-Dimethoxyphenyl)-vinyl]-1H-benzoimidazole-5-carboxylic acid methyl ester (3.5 g; 11 mmol) in MeOH (75 mL) and 2.5N NaOH solution (7.5 mL) was refluxed for 3 hours. The reaction mixture was cooled to ambient temperature and stirred for 18 hours. The reaction mixture was concentrated to dryness. The residue was dissolved in $H_2O$, and acidified with 2N HCl. Precipitate was collected. Recrystallization from MeOH gave 600 mg (15%) of the title compound as creamy solid, monohydrochloride, m.p. over 285° C. Anal. Calcd. for $C_{18}H_{16}N_2O_4$·HCl: C, 59.92, H, 4.75; N, 7.76. Found: C, 59.62; H, 4.80; N, 7.66. Mass spectrum: (EI; M$^+$) m/z 324. $^1$H-NMR (DMSO-d$_6$; 400 MHz) δ13.5(broad s, 1H), 8.24 (d, 1H), 8.14–8.2 (d, 1H), 8.02–8.06 (dd, 1H), 7.8 (d, 1H), 7.34 (d 1H), 7.26–7.28 (dd, 1H), 7.2–7.24 (d, 1H), 7.1 (d, 1H), 3.87 (s, 3H), 3.83 ppm (s, 3H).

EXAMPLE 7

(E)-2-[2-(3,4-Dimethoxyphenyl)-vinyl]-5-nitro-1H-benzoimidazole

A mixture of 4-nitro-1,2-phenylenediamine (1.2 g; 8 mmol) and methyl-(3,4-dimethoxy)-cinnamoimidate hydrochloride (2.0 g; 8 mmol) in methanol (70 mL) was refluxed for 18 hours. Solution was concentrated to dryness. The residue was recrystallized from MeOH to obtain 603 mg (23% yield) of the title compound as a yellow solid, m.p. 223–225° C. Anal. Calcd. for $C_{17}H_{15}N_3O_4$: C, 62.76, H, 4.65; N, 12.92. Found: C, 62.67; H, 4.62; N, 13.05. Mass spectrum: (EI; M$^+$) m/z 325. $^1$H-NMR (DMSO-d$_6$; 400 MHz) δ13.2(broad s, 1H), 8.4 (broad s, 1H), 8.1(dd, 1H), 7.74 (s, 1H), 7.62–7.72 (m, 1H), 7.35 (d 1H), 7.19–7.23 (dd, 1H), 7.17 (s, 1H), 7.0 (d,1H),3.85 (s, 3H), 3.8 ppm (s, 3H).

EXAMPLE 8

4-{2-[2-(3,4-Dimethoxyphenyl)-vinyl]-4,7-dimethoxy-5,6-dimethyl-benzoimidazol-1-ylmethyl}-benzoic acid methyl ester To a suspension of sodium hydride, 60% dispersion in oil (150 mg; 3.5 mmol) in 20 mL of DMF, {2-[2-(3,4-dimethoxyphenyl)-vinyl]-4,7-dimethoxy-5,6-dimethyl-1H-benzoimidazole (1.2 g; 3.25 mmol) in DMF (20 mL) was added dropwise over 5 minutes. After addition, the reaction mixture was stirred at ambient temperature for 30 minutes, then methyl-4-(bromomethyl)benzoate (745 mg; 3.25 mmol) in DMF (10 mL) was added. The reaction mixture was stirred at ambient temperature for 4 hours. The DMF was concentrated to a residue, and $H_2O$ was added. The solid was collected by filtration. Recrystallization from MeOH gave 620 mg (37% yield) of the title compound as a light yellow solid, hemihydrate, m.p. 111–114° C. Anal. Calcd. for $C_{30}H_{32}N_2O_6$—0.5 $H_2O$: C, 68.56, H, 6.33; N, 5.33. Found: C, 68.51; H, 6.27; N, 5.28. Mass spectrum: (EI; M$^+$) m/z 516.$^1$H-NMR (DMSO-d$_6$; 400 MHz) δ7.9(d, 2H), 7.72–7.78(d, 1H), 7.31(d, 1H), 7.2–7.26 (m, 4H), 6.95 (d, 1H), 5.9 (s, 2H), 4.12 (s, 3H), 3.81 (s 3H), 3.79 (s, 3H),3.77 (s, 3H), 3.53 (s, 3H), 2.1 ppm (d, 6H).

EXAMPLE 9

2-[2-(3,4-Dimethoxyphenyl)-vinyl]-5,6-dimethyl-1-benzoimidazol-4,7-dione

To a solution of 2-[2-(3,4-dimethoxyphenyl)-vinyl]-4,7-dimethoxy-5,6-dimethyl-1H-benzoimidazole (2.0 g; 5.4 mmol) in acetic acid (15 mL), ammonium cerium nitrate (7.25 g; 13 mmol) in 15 mL ($H_2O/CH_3CN$; 3/12) was added dropwise. The reaction mixture was heated at 40° C. for 1 hour. After cooling, the solid was filtered off, and the filtrate was concentrated to dryness, mixed with water and filtered. The red solid was dried at 60° C. under vacuum, suspended in MeOH and treated with hydrogen chloride to give 243 mg (13.5% yield) of the title compound as dark brown solid, quarter hydrate, m.p. 248° C. dec. Anal. Calcd. for $C_{19}H_{18}N_2O_4$—0.25 $H_2O$: C, 66.68, H, 5.33; N, 8.22. Found: C, 66.84; H, 5.32;N, 8.09. Mass spectrum: (EI; M+) m/z 338. 1H-NMR (DMSO-d6; 400 MHz) δ, 7.6–7.67 (d, 1H), 7.22(d, 1H), 7.1–7.14 (dd, 1H), 6.9–7.0 (d 1H), 6.94–6.98 (d, 1H), 3.82 (s, 3H), 3.78 (s, 3H), 1.9 ppm (s, 6H).

EXAMPLE 10

(E)-5-Nitro2-(2-pyridin-4-yl-vinyl)-1H-benzoimidazole

A mixture of 4-pyridyl acrylic acid (1.6 g; 10 mmol), 4-nitro-1,2-phenylene-diamine (1.5 g; 10 mmol) and polyphosphoric acid (15 g) was heated at 110° C. for 2.5 hours. The reaction mixture was cooled to 50° C., then poured into ice-$H_2O$ (100 mL). Insoluble material was filtered off and the filtrate was basified to pH 8 with ammonium hydroxide. The solid (2.3 g) was subjected to flash chromatography on silica gel ($CH_2Cl_2$/MeOH; 9:1) to afford 735 mg (28% yield) of the title compound as a yellow solid, m.p. above 280° C. Anal. Calcd. for $C_{14}H_{10}N_4O_2$: C, 63.15; H, 3.79; N, 21.04. Found: C, 62.92, H, 3.78; N, 21.08. Mass Spectrum: (EI; M$^+$) m/z 266. $^1$H-NMR (DMSO-d$_6$; 400 MHz) δ13.44 (broad s, 1H) 8.63 (dd, 2H), 8.35–8.55 (broad d, 1H), 8.03–8.18 (broad s, 1H), 7.69–7.83 (broad d, 2H), 7.65–7.7 (dd, 2H) 7.52–7.59 ppm (s, 1H).

EXAMPLE 11

Step 1

2-Furanacryloimidate hydrochloride

A solution of 2-furanacrylonitrile (10.9 g; 91 mmol) in EtOH (75 mL) was cooled in an ice bath. The cold mixture was then saturated with hydrogen chloride. The reaction solution was refrigerated for 18 hours. The reaction mixture was concentrated to 20 mL and diethyl ether was added. The brown solid gave 10.5 g (63% yield) of 2-Furanacryloimidate hydrochloride which was used in the next reaction.

Step 2

(E)-2-(2-Furan-3-yl-vinyl)-5-nitro-1H-benzoimidazole

A mixture of 4-nitro-1,2-phenylenediamine (1.53 g; 10 mmol) and 2-furanacryloimidate hydrochloride (2.21g; 11 mmol) in ethanol (50 mL) was refluxed for 4 hours. Solution was concentrated to dryness. The residue was dissolved in MeOH and treated with charcoal, to obtain 660 mg (25% yield) of the title compound as a yellow solid, m.p. 230–233° C. Anal. Calcd. for $C_{13}H_9N_3O_3$: C, 61.18, H, 3.55; N, 16.46. Found: C, 60.97; H, 3.29; N, 16.15. Mass spectrum: (EI; $M^+$) m/z 255. $^1$H-NMR (DMSO-$d_6$; 400 MHz) δ13.2(broad s, 1H), 8.4 (broad s, 1H), 8.1(dd, 1H), 7.9 (d, 1H), 7.62–7.8 (m, 2H), 6.92–7.0 (d 1H), 6.88(d, 1H), 6.6 ppm (d, 1H).

What is claimed is:

1. A compound of formula I:

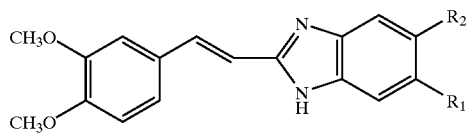

I wherein
$R_1$ and $R_2$ are hydrogen, halogen, alkyl of 1 to 6 carbon atoms, alkoxy of 1 to 6 carbon atoms, nitro, carboxyl, alkoxycarbonyl of 2 to 7 carbon atoms or aryloxycarbonyl of 7 to 12 carbon atoms;
or a pharmaceutically acceptable salt thereof.

2. A compound of claim 1 which is (E)-2-[2-(3,4-dimethoxyphenyl)-vinyl]-1H-benzoimidazole or a pharmaceutically acceptable salt thereof.

3. A compound of claim 1 which is 2-[2-(3,4-dimethoxyphenyl)-vinyl]-5-methoxy-1H-benzoimidazole or a pharmaceutically acceptable salt thereof.

4. A compound of claim 1 which is {2-[2-(3,4-dimethoxyphenyl)-vinyl]-1H-benzoimidazol-5-yl}-phenyl-methanone or a pharmaceutically acceptable salt thereof.

5. A compound of claim 1 which is (E)-2-[2-(3,4-dimethoxyphenyl)-vinyl]-1H-benzoimidazole-5-carboxylic acid methyl ester or a pharmaceutically acceptable salt thereof.

6. A compound of claim 1 which is (E)-2-[2-(3,4-dimethoxyphenyl)-vinyl]-1H-benzoimidazole-5-carboxylic acid or a pharmaceutically acceptable salt thereof.

7. A compound of claim 1 which is (E)-2-[2-(3,4-dimethoxyphenyl)-vinyl]-5-nitro-1H-benzoimidazole or a pharmaceutically acceptable salt thereof.

8. A pharmaceutical composition comprising a compound of formula I:

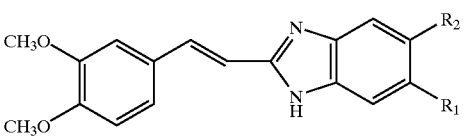

I wherein
$R_1$ and $R_2$ are hydrogen, halogen, alkyl of 1 to 6 carbon atoms, alkoxy of 1 to 6 carbon atoms, nitro, carboxyl, alkoxycarbonyl of 2 to 7 carbon atoms or aryloxycarbonyl of 7 to 12 carbon atoms;
or a pharmaceutically acceptable salt thereof, and a pharmaceutically acceptable carrier.

9. A method for preventing smooth muscle cell proliferation in a mammal which comprises administering to that mammal, orally or parenterally, a smooth muscle cell proliferation preventing amount of a compound of formula I or II:

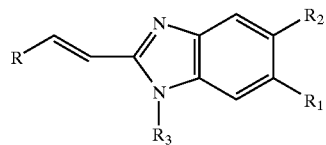

I

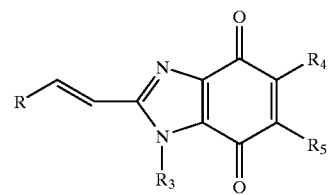

II wherein
R is phenyl or phenyl substituted with halogen, hydroxyl, alkoxy of 1 to 6 carbon atoms, alkyl of 1 to 6 carbon atoms, trifluoromethyl, or R is furyl, pyridyl or quinolinyl;
$R_1$ and $R_2$ are hydrogen, halogen, alkyl of 1 to 6 carbon atoms, alkoxy of 1 to 6 carbon atoms, nitro, carboxyl, alkoxycarbonyl of 2 to 7 carbon atoms or aryloxycarbonyl of 7 to 12 carbon atoms;
$R_3$ is hydrogen, alkyl of 1 to 6 carbon atoms, aryl of 6 to 12 carbon atoms or arylalkyl of 7 to 12 carbon atoms;
$R_4$ and $R_5$ are hydrogen or alkyl of 1 to 6 carbon atoms;
or a pharmaceutically acceptable salt thereof.

10. A method of claim 9 in which said compound is {2-[2-(3,4-dimethoxyphenyl)-vinyl]-1H-benzoimidazol-5-yl}-phenyl-methanone or a pharmaceutically acceptable salt thereof.

11. A method according to claim 9 wherein said smooth muscle cell proliferation manifests itself as restenosis following angioplasty.

* * * * *